United States Patent
Zhao et al.

(10) Patent No.: US 12,331,272 B1
(45) Date of Patent: Jun. 17, 2025

(54) ULTRA-HIGH-CELL-DENSITY MULTICELLULAR TISSUE LIFTING BIOPRINTING DEVICE ASSISTED BY OBLIQUE INCIDENT BULK WAVE AND PRINTING METHOD THEREFOR

(71) Applicant: NANJING DRUM TOWER HOSPITAL, Nanjing (CN)

(72) Inventors: Yuanjin Zhao, Nanjing (CN); Zhuhao Wu, Nanjing (CN)

(73) Assignee: NANJING DRUM TOWER HOSPITAL, Nanjing (CN)

( * ) Notice: Subject to any disclaimer, the term of this patent is extended or adjusted under 35 U.S.C. 154(b) by 0 days.

(21) Appl. No.: 18/988,990

(22) Filed: Dec. 20, 2024

Related U.S. Application Data (63) Continuation of application No. PCT/CN2024/087486, filed on Apr. 12, 2024.

(30) Foreign Application Priority Data

Mar. 18, 2024 (CN) .......................... 202410304987.X (51) Int. Cl.
| | |
|---|---|
| C12M 3/00 | (2006.01) |
| B29C 64/124 | (2017.01) |
| B29C 64/255 | (2017.01) |
| B33Y 10/00 | (2015.01) |
| B33Y 30/00 | (2015.01) |
| C12M 1/42 | (2006.01) |

(52) U.S. Cl.
CPC ........... *C12M 21/08* (2013.01); *B29C 64/124* (2017.08); *B29C 64/255* (2017.08); *B33Y 10/00* (2014.12); *B33Y 30/00* (2014.12); *C12M 35/04* (2013.01)

(58) Field of Classification Search
None
See application file for complete search history.

(56) References Cited

U.S. PATENT DOCUMENTS

| | | | |
|---|---|---|---|
| 2021/0154368 A1 | 5/2021 | Alsberg et al. | |
| 2021/0260578 A1 | 8/2021 | Shirwaiker et al. | |
| 2024/0043825 A1* | 2/2024 | Bailey .................... | C12N 13/00 |

FOREIGN PATENT DOCUMENTS

| | | |
|---|---|---|
| CN | 106725999 A | 5/2017 |
| CN | 109311226 A | 2/2019 |
| CN | 111826262 A | 10/2020 |
| CN | 112538426 A | 3/2021 |
| CN | 113601834 A | 11/2021 |
| CN | 113941030 A | 1/2022 |
| CN | 115772491 A | 3/2023 |
| CN | 116148453 A | 5/2023 |
| CN | 116851048 A | 10/2023 |

OTHER PUBLICATIONS

Guex et al. "The waves that make the pattern: a review on acoustic manipulation in biomedical research" (2021) Material Today Bio, vol. 10, paper No. 1000110 (Year: 2021).*
Chen et al. "Multimaterial 3D and 4D Bioprinting of Heterogenous Construct for Tissue Engineering" (2024) Adv Mater, vol. 36, No. 2307686 (Year: 2024).*
Lee et al. "Guiding Lights: Tissue Bioprinting Using Photoactivated Materials" (2020) Chem Rev, vol. 120: 10950-11027. (Year: 2020).*

* cited by examiner

*Primary Examiner* — Teresa E Knight
(74) *Attorney, Agent, or Firm* — Bayramoglu Law Offices LLC (57) ABSTRACT

An ultra-high-cell-density multicellular tissue lifting bioprinting device assisted by oblique incident bulk wave and a printing method therefor are provided, and the printing device includes a printing liquid tank, a printing platform, a light source and an oblique incident bulk wave chip; the printing liquid tank contains a printing liquid which is a mixture of cells and a photocurable bioink; the printing platform is arranged horizontally and extends into the printing liquid tank to come into contact with the printing liquid; the printing platform is capable of going up and down; the light source is arranged under the printing liquid tank, and light enters the printing liquid tank; the oblique incident bulk wave chip is a piezoelectric transducer arranged obliquely; the piezoelectric transducer is arranged under the printing liquid tank and tilted relative to the horizontal plane to generate an oblique incident bulk wave acoustic field in the printing liquid.

16 Claims, 6 Drawing Sheets

FIG. 4B

ULTRA-HIGH-CELL-DENSITY MULTICELLULAR TISSUE LIFTING BIOPRINTING DEVICE ASSISTED BY OBLIQUE INCIDENT BULK WAVE AND PRINTING METHOD THEREFOR

CROSS REFERENCE TO THE RELATED APPLICATIONS

This application is a continuation application of International Application No. PCT/CN2024/087486, filed on Apr. 12, 2024, which is based upon and claims priority to Chinese Patent Application No. 202410304987.X, filed on Mar. 18, 2024, the entire contents of which are incorporated herein by reference.

TECHNICAL FIELD

The present invention belongs to the technical field of medical manufacturing and relates to a bioprinting device, in particular to an ultra-high-cell-density multicellular tissue lifting bioprinting device assisted by oblique incident bulk wave and a printing method therefor.

BACKGROUND

Solid organs play a vital role in maintaining the physiological stability of the human bulk, and the specific functions of these bulk organs depend on the tight biological contact of cells at the nanometer and micron level formed by special development. The bionic reconstruction of organs is an important research field with important practical significance. Various technologies have been developed to reconstruct organs and tissues with the aim of recreating their functional characteristics. Among them, three-dimensional (3D) bioprinting uses biological inks, cells and additive manufacturing to create bionic living systems and has the unique advantages of high precision, multi-dimension, high degree of freedom, high throughput and integration compared with other organ engineering technologies.

Extrusion or traction jet technology and lithography by light, heat or ultrasonic polymerization are the main strategies for 3D bioprinting. Jet-based bioprinting can realize the controlled deposition of cell-filled bioinks in the form of droplets and fibers via a nozzle or print head, allowing bottom-up engineering of living structures with precise cell types and arrangements. Lithography-based bioprinting can induce layer by layer cross-linking of materials by projecting images onto photosensitive biomaterials, resulting in more complex 3D biological structures. This method can precisely and flexibly control tissue size and shape, providing ultra-high resolution. Compared with solid natural tissues (cell density is generally greater than 40 million cells/ml), these traditional printing methods cannot achieve ultra-high cell density. Because mechanical extrusion or traction of high-cell-density bioinks in jet-based bioprinting often leads to cell damage, and the lack of effective and controllable cell assembly strategies in lithography-based bioprinting, these bottlenecks limit the application of traditional 3D bioprinting.

SUMMARY

Aiming at the problem of low cell density of conventional 3D bioprinting, the present invention provides an ultra-high-cell-density multicellular tissue lifting bioprinting device assisted by oblique incident bulk wave and a printing method therefor, which can be used to produce multicellular bionic in-vitro tissues with real organ density, and can be applied to drug screening, disease research, organ transplantation and other fields.

To fulfill the above purpose, the present invention provides an ultra-high-cell-density multicellular tissue lifting bioprinting device assisted by oblique incident bulk wave, which has such characteristics: including a printing liquid tank, a printing platform, a light source and an oblique incident bulk wave chip; the printing liquid tank contains a printing liquid which is a mixture of cells and a photocurable bioink; the bioink may be a photocurable reagent such as a hydrogel solution; the printing platform is arranged horizontally and extends into the printing liquid tank to come into contact with the printing liquid (the printing platform may be in contact with the liquid level of the printing liquid or extend into the printing liquid to realize the contact); the printing platform is capable of going up and down; the light source is arranged under the printing liquid tank, and light enters the printing liquid tank to solidify the printing liquid; the oblique incident bulk wave chip is a piezoelectric transducer arranged obliquely; the piezoelectric transducer is arranged under the printing liquid tank and tilted relative to the horizontal plane, pointing to the center of the printing liquid tank, to generate an oblique incident bulk wave acoustic field in the printing liquid.

Preferably, the present invention provides an ultra-high-cell-density multicellular tissue lifting bioprinting device assisted by oblique incident bulk wave, which further has such characteristics: wherein, the tilt angle of the piezoelectric transducer satisfies is between 0° and 90°, preferably 45°.

Preferably, the present invention provides an ultra-high-cell-density multicellular tissue lifting bioprinting device assisted by oblique incident bulk wave, which further has such characteristics: wherein, the piezoelectric transducer is configured as piezoelectric ceramic, positive and negative electrodes are welded on a same side of the piezoelectric ceramic, and a driving signal is a sinusoidal AC input with a voltage of 200 mVpp.

Preferably, the present invention provides an ultra-high-cell-density multicellular tissue lifting bioprinting device assisted by oblique incident bulk wave, which further has such characteristics: wherein, the operating frequency of the piezoelectric transducer is 1-10 MHZ, preferably 2.06 MHz.

Preferably, the present invention provides an ultra-high-cell-density multicellular tissue lifting bioprinting device assisted by oblique incident bulk wave, which further has such characteristics: wherein, the piezoelectric transducer is arranged in a medium capable of conducting acoustic wave.

Preferably, the present invention provides an ultra-high-cell-density multicellular tissue lifting bioprinting device assisted by oblique incident bulk wave, which further has such characteristics: wherein, the printing device further includes an acoustic wave medium container; the acoustic medium container is arranged under the printing liquid tank and contains the medium capable of conducting acoustic wave; the piezoelectric transducer is arranged in an acoustic medium container.

Preferably, the present invention provides an ultra-high-cell-density multicellular tissue lifting bioprinting device assisted by oblique incident bulk wave, which further has such characteristics: wherein, the printing device further includes a lifting platform; the printing platform is fixed under the lifting platform, and the lifting platform drives the printing platform to go up and down.

The present invention further provides a printing method for the ultra-high-cell-density multicellular tissue lifting bioprinting device assisted by oblique incident bulk wave, which has such characteristics: a printing method for a single-layer tissue includes the following steps: S1.1, performing exposure by the light source to obtain a toroidal projection so that the printing liquid solidifies to form a toroidal acoustic field boundary; S1.2, activating the oblique incident bulk wave chip to form an oblique incident bulk wave acoustic field, and causing a fluid vortex within the acoustic field boundary to aggregate the cells in the printing liquid; S1.3, performing exposure by the light source to obtain a projection of a shape to be printed so that the printing liquid solidifies into a tissue containing aggregated cells in the shape to be printed; S1.4, performing exposure by the light source to obtain a projection of the shape containing the printed tissue so that the printing liquid solidifies into a single-layer print structure containing the tissue from step S1.3.

Preferably, the present invention provides a printing method for the ultra-high-cell-density multicellular tissue lifting bioprinting device assisted by oblique incident bulk wave, which further has such characteristics: wherein, a printing method for a multi-layer tissue includes the following steps: S1, printing a single-layer print structure according to the printing method for a single-layer tissue firstly; S2, lifting the printing platform up, repeating steps S1.1 to S1.4 to print a second layer of print structure under the single-layer print structure; S3, repeating step S2 n times to obtain (n+2) layers of print structure, where n≥0.

Preferably, the present invention provides a printing method for the ultra-high-cell-density multicellular tissue lifting bioprinting device assisted by oblique incident bulk wave, which further has such characteristics: wherein, a distance between the printing platform and a bottom surface of the printing liquid tank is the thickness of the print structure at the corresponding layer.

The present invention has the advantages that: the present invention discloses an ultra-high-cell-density multicellular tissue lifting bioprinting device assisted by oblique incident bulk wave and printing method therefor, which can realize the large-volume 3D printing of a bionic tissue model with an ultra-high cell density and a multicellular structure. The present invention is a cell manipulation method with a bulk acoustic wave fluid as the main bulk, which can control cells remotely without contact, and realize the rapid increase of cell density. Specifically, according to the present invention, the cells are aggregated in a pre-polymerized central area based on a large-volume eddy current caused by the oblique incident bulk wave, thus obtaining a cell hydrogel carrier with a cell density comparable to that of natural tissue. Then, through the integrated lifting stereolithography process, the bionic cell structure with 3D complex layers can be generated. The present invention can realize an architecture of arbitrary multicellular components by incorporating an acoustically assisted medium exchange system.

Specifically, in the present invention, a vortex is generated by the oblique incident bulk wave and the toroidal acoustic field boundary. First, the piezoelectric sensor is activated to generate a plane wave, which then enters the printing liquid tank at an oblique incidence. Due to the attenuation effect of the acoustic wave, the directional flow of the printing liquid in the printing liquid tank will be caused in the propagation direction of the plane wave, which is manifested in the form of liquid pulse. Then, the liquid pulse is constrained by the toroidal acoustic field boundary to form a vortex-shaped liquid flow. Finally, driven by this vortex, the cells in the printing liquid are enriched in a central region of the printing liquid tank, thus achieving a significant dynamic enhancement of cell density.

The present invention can significantly improve the cell aggregation flux caused by acoustic wave, increase the cell concentration in the hydrogel, and also realize the rapid construction of highly bionic multicellular organs, and has the advantages of ultra-high speed, large volume, adjustable cell concentration and simple liquid exchange structure.

BRIEF DESCRIPTION OF THE DRAWINGS

FIGS. 1A-1B are schematic structural diagrams of an ultra-high-cell-density multicellular tissue lifting bioprinting device assisted by oblique incident bulk wave.

FIGS. 2A-2B show two-dimensional cell aggregation.

FIGS. 3A-3B show a multicellular printing process: FIGS. 4A-4B are physical pictures of a printed ultra-high-density multicellular tissue.

DETAILED DESCRIPTION OF THE EMBODIMENTS

The specific embodiments of the present invention are described below in conjunction with the accompanying drawings.

Figure 1A:
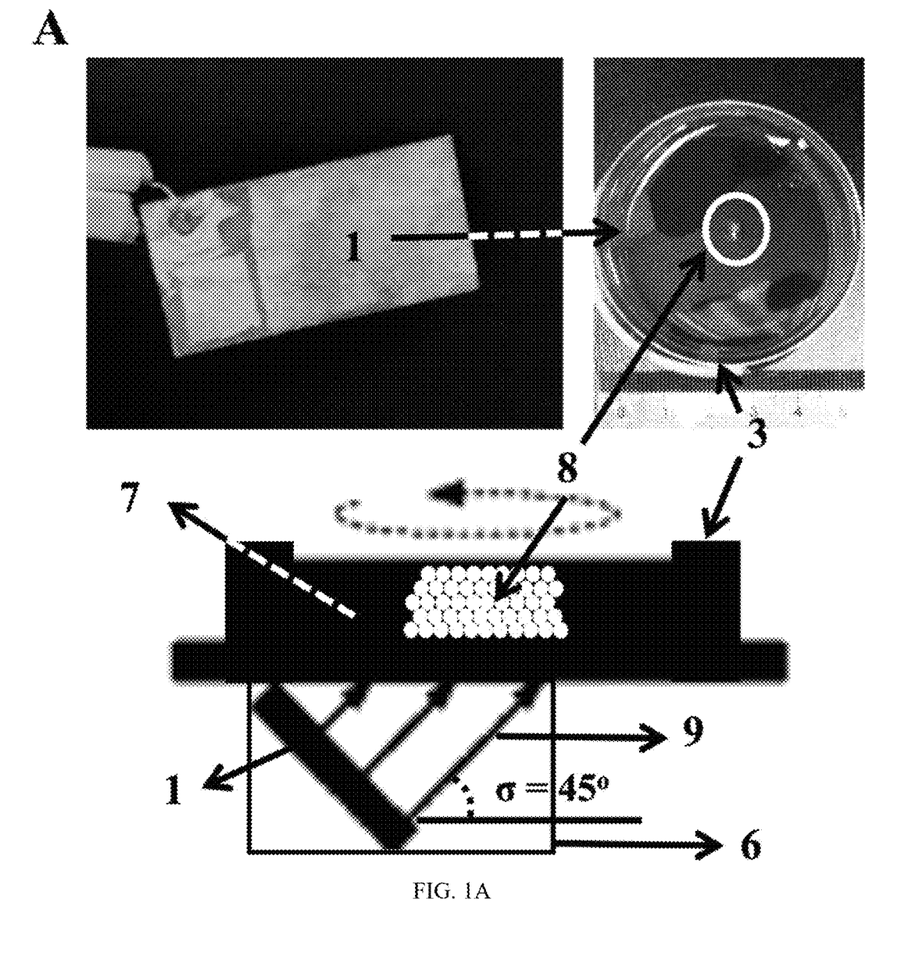
(FIG. 1A) physical picture of the oblique incident bulk wave chip and schematic diagram of the formation of the oblique incident bulk wave acoustic field.
Figure 1B:
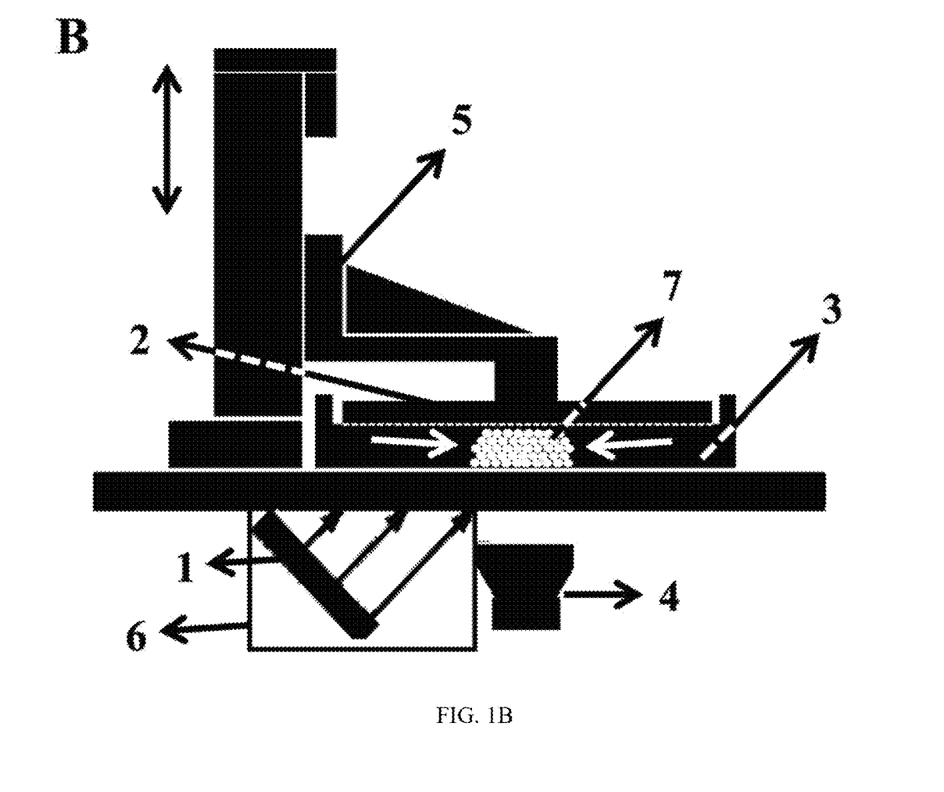
(FIG. 1B) schematic structural diagram of the printing device: 1. oblique incident bulk wave chip; 2. printing platform; 3. printing liquid tank; 4. light source; 5. lifting platform; 6. acoustic medium container; 7. printing liquid; 8. vortex acoustic streaming caused by the bulk wave; 9. incident acoustic wave.

As shown in FIGS. 1A-1B, the present invention provides an ultra-high-cell-density multicellular tissue lifting bioprinting device assisted by oblique incident bulk wave, including an oblique incident bulk wave chip 1, a printing platform 2, a printing liquid tank 3 and a light source.

The printing liquid tank 3 contains a printing liquid 7 which is a mixture of cells and a photocurable bioink. The bioink may be a photocurable reagent such as a hydrogel solution.

The printing platform 2 is arranged horizontally and extends into the printing liquid tank 3 to come into contact with the printing liquid. Specifically, the printing platform 2 may be in contact with the liquid level of the printing liquid or extend into the printing liquid to realize the contact.

The printing platform 2 is capable of going up and down. Specifically, the printing device may includes a lifting platform 5. The printing platform 2 is fixed under the lifting platform 5, and the lifting platform 5 drives the printing platform 2 to go up and down.

The light source 4 is arranged under the printing liquid tank 3, and light enters the printing liquid tank 3 to solidify the printing liquid.

The oblique incident bulk wave chip 1 is a piezoelectric transducer arranged obliquely. The piezoelectric transducer is arranged under the printing liquid tank 3 and tilted relative to the horizontal plane, pointing to the center of the printing liquid tank 3, to generate an oblique incident bulk wave acoustic field in the printing liquid. A tilt angle of the piezoelectric transducer is between 0° and 90°, preferably 45°. An operating frequency of the piezoelectric transducer is 1-10 MHZ, preferably 2.06 MHz. Specifically, the piezoelectric transducer is configured as piezoelectric ceramic. Positive and negative electrodes are welded on a same side of the piezoelectric ceramic, and a driving signal is a sinusoidal AC input with a voltage of 200 mVpp.

In some preferred embodiments, the piezoelectric transducer is arranged in a medium capable of conducting acoustic wave. Specifically, the printing device further includes an acoustic wave medium container 6. The acoustic medium container 6 is arranged under the printing liquid tank 3 and contains the medium capable of conducting acoustic wave; the piezoelectric transducer is arranged in an acoustic medium container 6, and the position where the piezoelectric transducer is arranged may be fixed by a rigid bracket printed by a 3D printer.

The present invention further provides a printing method for the ultra-high-cell-density multicellular tissue lifting bioprinting device assisted by oblique incident bulk wave.

A printing method for a single-layer tissue includes the following steps:
- S1.1, performing exposure by the light source to obtain a toroidal projection so that the printing liquid solidifies to form a toroidal acoustic field boundary.
- S1.2, activating the oblique incident bulk wave chip to form an oblique incident bulk wave acoustic field, and causing a fluid vortex within the acoustic field boundary to aggregate the cells in the printing liquid;
- S1.3, performing exposure by the light source to obtain a projection of a shape to be printed so that the printing liquid solidifies into a tissue containing aggregated cells in the shape to be printed; and
- S1.4, performing exposure by the light source to obtain a projection of the shape containing the printed tissue so that the printing liquid solidifies into a single-layer print structure containing the tissue from step S1.3.

A printing method for a multi-layer tissue includes the following steps:
- S1, printing a single-layer print structure according to the printing method for a single-layer tissue firstly;
- S2, lifting the printing platform up, repeating steps S1.1 to S1.4 to print a second layer of print structure under the single-layer print structure; and
- S3, repeating step S2 n times to obtain (n+2) layers of print structure, where n≥0.

A distance between the printing platform and a bottom surface of the printing liquid tank is the thickness of the print structure at the corresponding layer. That is, in step S1, the distance between the printing platform and the bottom surface of the printing liquid tank is the thickness of the printed single-layer tissue; in step S2, the lifting distance of the printing platform is the thickness of the printed structure at the corresponding layer.

In the present invention, a bulk wave is generated by the piezoelectric transducer arranged obliquely, and a liquid vortex is formed by a toroidal boundary. By adjusting the spatial position and the liquid boundary conditions of the oblique incident bulk wave acoustic field, the phenomenon of cell aggregation in a large range of liquid is realized. By adjusting the intensity of the acoustic field, the thickness of the liquid layer and the initial cell concentration, different cell aggregation speeds, areas and degrees are obtained. Specifically, the oblique incident bulk wave chip can produce stable focused acoustic streaming, thereby achieving cell enrichment in a central region in the liquid. Increasing or decreasing the input power intensity of the signal of the oblique incident bulk wave chip, the focused acoustic streaming will speed up or slow down, and the time and range of cell enrichment in the central region will increase or decrease accordingly. When the directional deflection angle of the piezoelectric transducer of the oblique incident bulk wave chip is changed, the corresponding focused acoustic streaming will also change, so as to control the aggregation state of the cells. The design and preparation method of the oblique incident bulk wave chip is as follows: firstly, the finite element analysis simulation computer software COMSOL is used to design and optimize the acoustic streaming caused by the piezoelectric transducer in the printing liquid tank, and then the control variable experiment is used to verify the effect. The oblique incident bulk wave chip is directly incident from the bottom of the lift printer obliquely, without affecting the propagation and projection of the projection light source.

Through the optimized oblique incident bulk wave chip and the integration of the lift stereolithography process, the cells in the photocrosslinkable bioink in stereolithography can be concentrated and concentrated in a remotely controllable manner, so as to achieve ultra-high-density 3D bioprinting. For example, the adjustable-density spatial structure of one or more kinds of vascular endothelial cells, smooth muscle cells and fibroblasts can be constructed, and also the vascular structure can be realized inside the spatial structure. The printing area reaches the centimeter level, which greatly improves the printing efficiency and speed.

In a specific embodiment, a piezoelectric transducer of 0.5×5×10 mm with an operating frequency of 2.06 MHz is placed under a lift printer, pointing to the center of the liquid tank with a clockwise deflection angle of 45°, to form an oblique incident bulk wave chip. The printing liquid is added in the printing liquid tank: 10% (v/v) gelatin, a photoinitiator Ruthenium (Ru)/sodium persulfate (SPS) (1 mM/10 mM) and cells at a density of one million cells per milliliter.

Figure 2A:
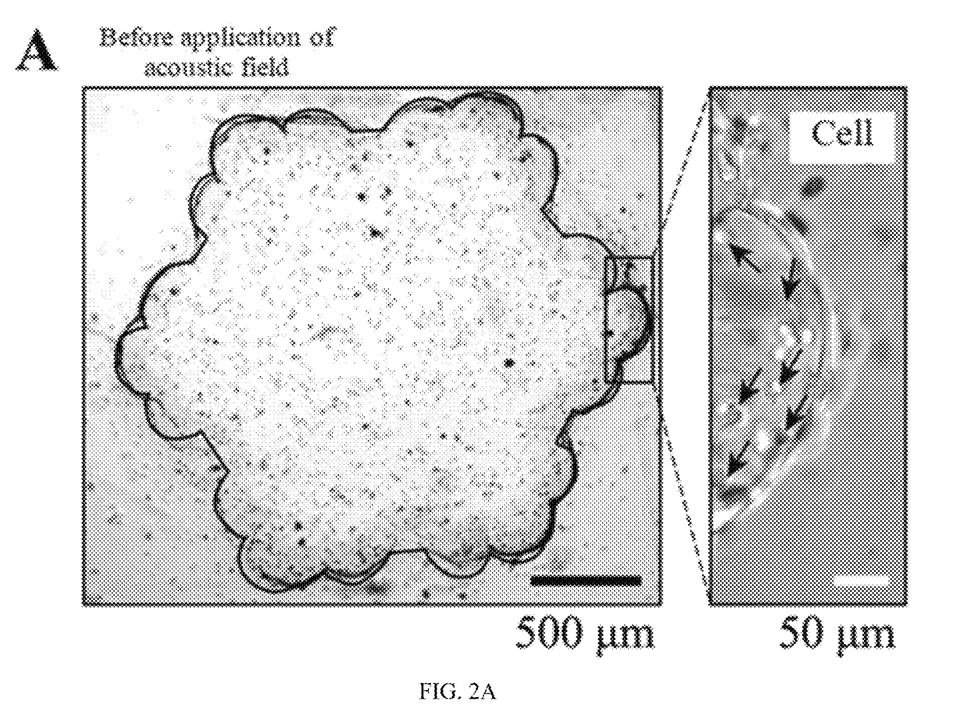
(FIG. 2A) sparse cell sheet before acoustic wave aggregation.
Figure 2B:
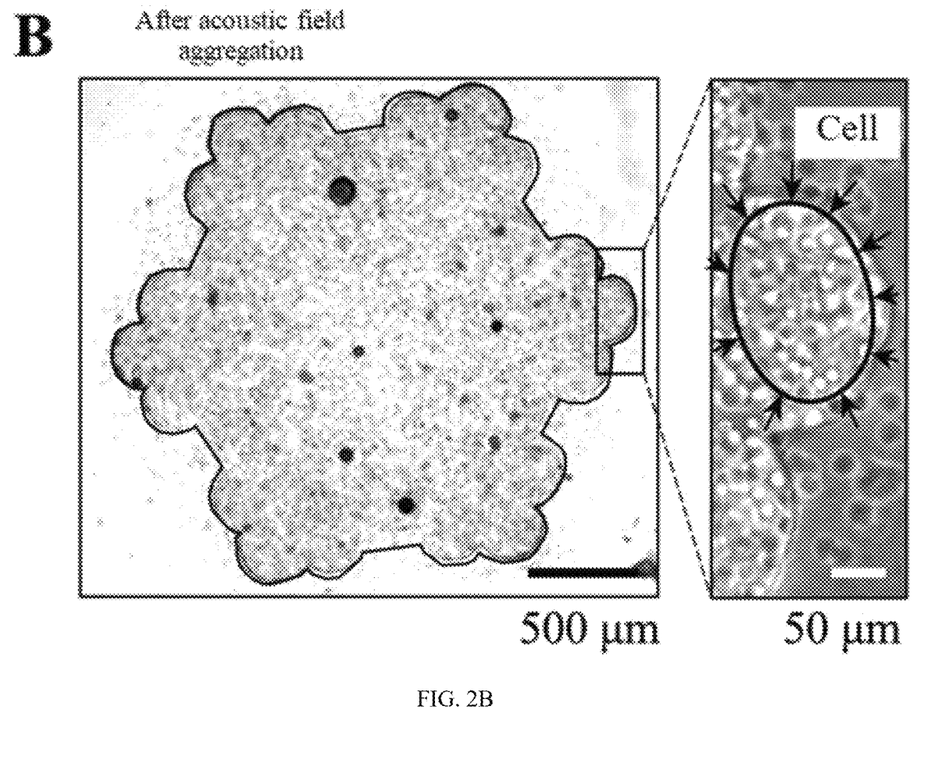
(FIG. 2B) high-density cell sheet after acoustic wave aggregation.

First, a toroidal hydrogel boundary (a toroidal acoustic field boundary) with a diameter of 4 cm is formed by exposure. Then, the acoustic field is excited. Within the toroidal hydrogel boundary with a diameter of 4 cm and driven by a sinusoidal AC electrical signal with a voltage of 200 mVpp, a liquid vortex is formed in the central region and continuously pulls cells. After 40 seconds of cell aggregation, cells in the central region form close contact. FIGS. 2A-2B show cells before and after cell aggregation. The structure to be printed is re-projected with an exposure time of 5 seconds and an exposure intensity of 60 mW/cm$^2$. Finally, the whole layer of the printing liquid containing cells is solidified to obtain a high-density two-dimensional cell gel sheet with high mechanical strength.

The printing platform is controlled by programming software to move down 40 μm for cell printing at the next layer. After cells set still for 15 seconds, the steps for printing the first layer are repeated: printing the acoustic field boundary, aggregating cells with acoustic fluid, patterning the polymerized bioink, and solidifying the whole layer of bioink. The same procedure is repeated round by round to result in a complex structure with a high cell density.

The device may also be equipped with multiple piezoelectric transducers arranged obliquely to adjust the rotation speed of the generated acoustic field vortex.

Figure 3A:
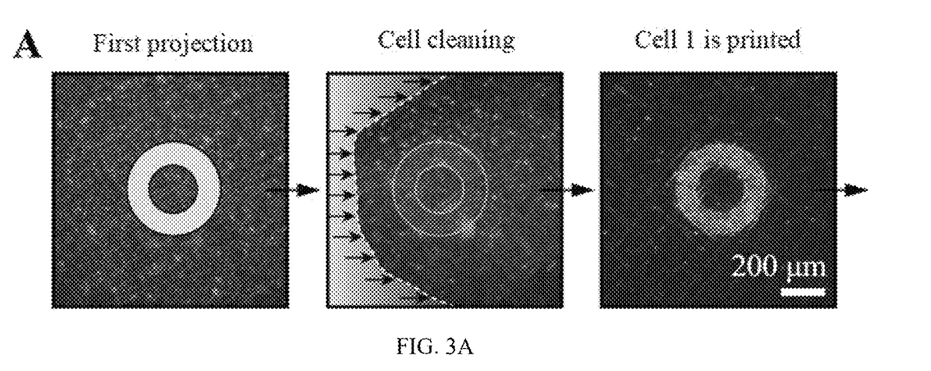
(FIG. 3A): first cell printing.
Figure 3B:
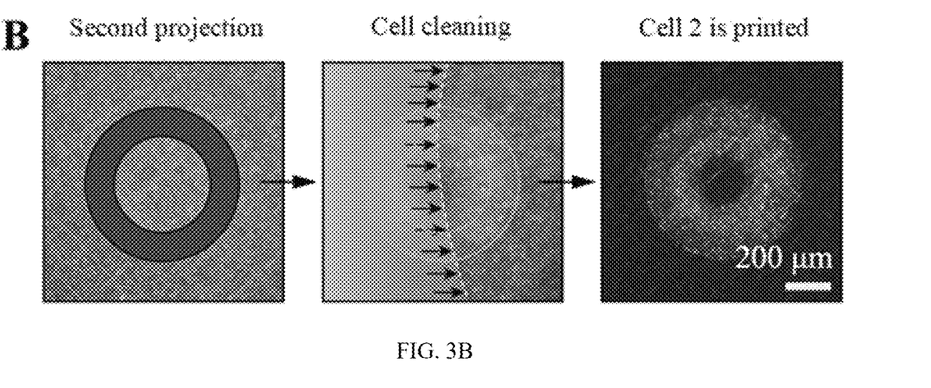
(FIG. 3B) second cell printing.

The device may also carry out multicellular printing, that is, cells in different layer structures are different. During printing, between operations for printing different layer structures, the printing liquid may be allowed to flow out of the printing liquid tank by turning on the piezoelectric transducer (no acoustic field boundary), and then another printing liquid is used for printing the next layer, as shown in FIGS. 3A-3B.

Figure 4A:
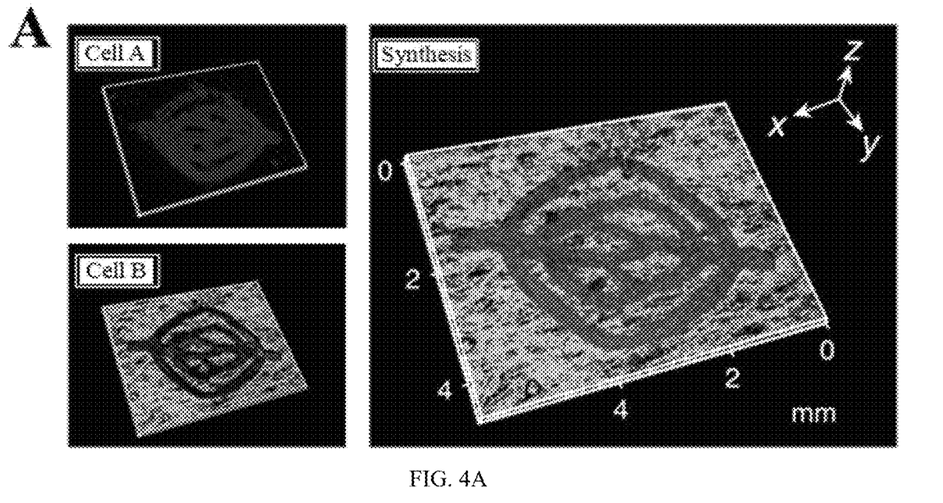
(FIG. 4A) 3D vascular structure.
Figure 4B:
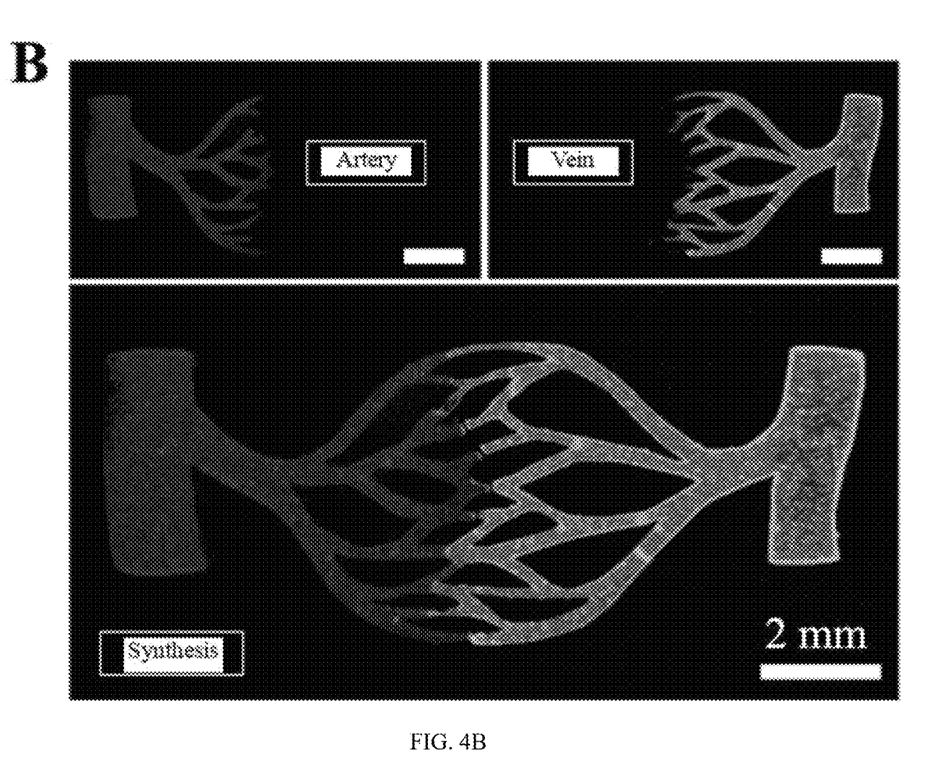
(FIG. 4B) artery and vein structures.

Cells of the target organ, such as vascular endothelial cells and smooth muscle cells, are used to print high-density bionic multicellular structures including vascular tissues; or, different vascular endothelial cells are used to print high-density bionic multicellular structures including arteriovenous tissues, as shown in FIGS. 4A-4B.

In the invention, unless otherwise stated, the scientific and technical terms used herein have meanings commonly understood by those skilled in the art. In addition, the reagents, materials and procedures used herein are reagents, materials and conventional procedures widely used in the corresponding field.

It should be noted that the terms cited in the invention, such as "up", "down", "left", "right", "front", "rear", are also for the convenience of clear description but not for limiting the scope of implementation of the invention, and the change or adjustment of their relative relationship shall also be regarded as falling within the scope of implementation of the invention without the material change of the technical content.

Finally, it should be noted that the above are only preferred embodiments of the invention and are not used to limit the invention. Although the invention is described in detail by reference to the above embodiments, it is still possible for a person skilled in the art to modify the technical solutions described in the above embodiments or make equivalent replacement to some of the technical features. Any modification, equivalent replacement, improvement, etc. made within the spirit and principle of the invention shall fall within the scope of the invention.

What is claimed is:

1. An ultra-high-cell-density multicellular tissue lifting bioprinting device assisted by oblique incident bulk wave, comprising:
    a printing liquid tank, a printing platform, a light source, and an oblique incident bulk wave chip, wherein
    the printing liquid tank contains a printing liquid, wherein the printing liquid is a mixture of cells and a photocurable bioink;
    the printing platform is arranged horizontally and extends into the printing liquid tank to come into contact with the printing liquid;
    the printing platform is configured for going up and down;
    the light source is arranged under the printing liquid tank, and light enters the printing liquid tank; and
    the oblique incident bulk wave chip is a piezoelectric transducer arranged obliquely; and the piezoelectric transducer is arranged under the printing liquid tank and tilted relative to a horizontal plane to generate an oblique incident bulk wave acoustic field in the printing liquid.

2. The ultra-high-cell-density multicellular tissue lifting bioprinting device according to claim 1, wherein a tilt angle of the piezoelectric transducer is between 0° and 90°.

3. The ultra-high-cell-density multicellular tissue lifting bioprinting device according to claim 1, wherein the piezoelectric transducer is configured as piezoelectric ceramic.

4. The ultra-high-cell-density multicellular tissue lifting bioprinting device according to claim 1, wherein an operating frequency of the piezoelectric transducer is 1 MHZ-10 MHZ.

5. The ultra-high-cell-density multicellular tissue lifting bioprinting device according to claim 1, wherein the piezoelectric transducer is arranged in a medium configured for conducting an acoustic wave.

6. The ultra-high-cell-density multicellular tissue lifting bioprinting device according to claim 5, further comprising an acoustic wave medium container; wherein
    the acoustic wave medium container is arranged under the printing liquid tank and contains the medium configured for conducting the acoustic wave; and the piezoelectric transducer is arranged in the acoustic wave medium container.

7. The ultra-high-cell-density multicellular tissue lifting bioprinting device according to claim 1, further comprising a lifting platform; wherein
    the printing platform is fixed under the lifting platform, and the lifting platform drives the printing platform to go up and down.

8. A printing method for the ultra-high-cell-density multicellular tissue lifting bioprinting device according to claim 1, wherein a printing method for a single-layer tissue comprises the following steps:
    S1.1, performing exposure by the light source so that the printing liquid solidifies to form a toroidal acoustic field boundary;
    S1.2, activating the oblique incident bulk wave chip to form the oblique incident bulk wave acoustic field, and causing a fluid vortex within the toroidal acoustic field boundary to aggregate the cells in the printing liquid to obtain aggregated cells;
    S1.3, performing the exposure by the light source so that the printing liquid solidifies into a tissue containing the aggregated cells in a shape to be printed; and
    S1.4, performing the exposure by the light source so that the printing liquid solidifies into a single-layer print structure containing the tissue from the step S1.3.

9. The printing method according to claim 8, wherein the method produces a multi-layer tissue and comprises the following steps:
    S1, printing the single-layer print structure according to the printing method for the single-layer tissue;
    S2, lifting the printing platform up, and repeating the steps S1.1 to S1.4 to print a second layer of print structure under the single-layer print structure; and
    S3, repeating the step S2 n times to obtain (n+2) layers of print structure, wherein n≥0.

10. The printing method according to claim 8, wherein a distance between the printing platform and a bottom surface of the printing liquid tank is a thickness of print structure at a corresponding layer.

11. The printing method according to claim 8, wherein in the ultra-high-cell-density multicellular tissue lifting bioprinting device, a tilt angle of the piezoelectric transducer is between 0° and 90°.

12. The printing method according to claim 8, wherein in the ultra-high-cell-density multicellular tissue lifting bioprinting device, the piezoelectric transducer is configured as piezoelectric ceramic.

13. The printing method according to claim 8, wherein in the ultra-high-cell-density multicellular tissue lifting bioprinting device, an operating frequency of the piezoelectric transducer is 1 MHZ-10 MHZ.

14. The printing method according to claim 8, wherein in the ultra-high-cell-density multicellular tissue lifting bioprinting device, the piezoelectric transducer is arranged in a medium configured for conducting an acoustic wave.

15. The printing method according to claim 14, wherein the ultra-high-cell-density multicellular tissue lifting bioprinting device further comprises an acoustic wave medium container; wherein the acoustic wave medium container is arranged under the printing liquid tank and contains the medium configured for conducting the acoustic wave; and the piezoelectric transducer is arranged in the acoustic wave medium container.

16. The printing method according to claim 8, wherein the ultra-high-cell-density multicellular tissue lifting bioprinting device further comprises a lifting platform; wherein the printing platform is fixed under the lifting platform, and the lifting platform drives the printing platform to go up and down.

* * * * *